(12) United States Patent
Sudol (10) Patent No.: US 7,637,869 B2
(45) Date of Patent: Dec. 29, 2009

(54) TWO-DIMENSIONAL TRANSDUCER ARRAYS FOR IMPROVED FIELD OF VIEW

(75) Inventor: Wojtek Sudol, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 400 days.

(21) Appl. No.: 10/560,722

(22) PCT Filed: Jun. 26, 2004

(86) PCT No.: PCT/IB2004/051016

§ 371 (c)(1),
(2), (4) Date: Dec. 15, 2005

(87) PCT Pub. No.: WO2005/001510

PCT Pub. Date: Jan. 6, 2005

(65) Prior Publication Data

US 2006/0173333 A1 Aug. 3, 2006

Related U.S. Application Data

(60) Provisional application No. 60/483,797, filed on Jun. 30, 2003.

(51) Int. Cl.
*A61B 8/00* (2006.01)
(52) U.S. Cl. ............... 600/437; 600/447; 600/459; 367/178
(58) Field of Classification Search ............ 73/625, 73/626; 600/437–466; 367/178
See application file for complete search history.

(56) References Cited

U.S. PATENT DOCUMENTS

| 5,640,371 A | 6/1997 | Priest et al. |
| 5,738,098 A * | 4/1998 | Brock-Fisher et al. ...... 600/472 |
| 5,798,461 A * | 8/1998 | Banta et al. .................. 73/625 |
| 5,938,612 A * | 8/1999 | Kline-Schoder et al. .... 600/459 |
| 6,055,861 A * | 5/2000 | Banta et al. .................. 73/626 |
| 6,381,197 B1 * | 4/2002 | Savord et al. ............... 367/178 |
| 6,682,483 B1 * | 1/2004 | Abend et al. ................ 600/437 |
| 7,238,158 B2 * | 7/2007 | Abend ......................... 600/454 |
| 2003/0011285 A1 | 1/2003 | Ossmann |

* cited by examiner

*Primary Examiner*—Long V Le
*Assistant Examiner*—Sanjay Cattungal

(57) ABSTRACT

A method and system for using two-dimensional transducer arrays for improving the field of view during an ultrasonic examination are disclosed. The ultrasonic imaging system includes a two-dimensional transducer array with a plurality of acoustic elements, a beam controller, a signal processor, and a display. The beam controller controls a generated acoustic beam capable of being advanced longitudinally or laterally along the two-dimensional transducer array. Additionally, the generated acoustic beam is capable of being phase-shifted by the beam controller. Combining the phase shifting of and advancement of the acoustic beam increases the field of view of the two-dimensional array.

25 Claims, 6 Drawing Sheets

TWO-DIMENSIONAL TRANSDUCER ARRAYS FOR IMPROVED FIELD OF VIEW

CROSS REFERENCE TO RELATED APPLICATIONS

This application claims benefit of U.S. provisional application Ser. No. 60/483,797 filed Jun. 30, 2003, which is incorporated herein by reference.

The present invention relates generally to transducers. More specifically, it relates to ultrasonic imaging systems using two-dimensional ultrasonic transducer arrays having an improved field of view.

Ultrasonic transducers are used in many medical applications and, in particular, for the non-invasive acquisition of images of organs and conditions within a patient, typical examples being the ultrasonic imaging of fetuses and the heart. The ultrasonic transducers used in such applications are generally hand held, and must meet stringent dimensional constraints in order to acquire the desired images. It is frequently necessary that the transducer be able to obtain high resolution images of particular portions of a patient's body when using endoscopic ultrasonic imaging equipment.

Typically, conventional ultrasonic imaging equipment use two-dimensional arrays for acquiring the ultrasonic images of particular tissues or organs within the patient's body. Generally, these arrays include a plurality of acoustic elements arranged in a planar configuration. Beam steering is used in such systems to control the propagation of the direction of the ultrasonic beam. Employing this method allows ultrasonic systems to acquire images of the particular region of the patient's body.

However, conventional ultrasonic systems have a limited field of view due to the limitations at the beam steering end due to the planar arrangement of the acoustic elements. Therefore, a need exists for an improved ultrasonic array for use with conventional ultrasonic imaging systems.

It is an object of the present invention is to provide an ultrasonic imaging system having improved volumetric imaging.

Another object of the present invention to provide an ultrasonic imaging system having an increased field of view.

Yet another object of the present invention is to provide an ultrasonic imaging system with improved ergonomic characteristics.

A further object of the present invention is to provide an ultrasonic imaging system that has particular characteristics of its acoustic pulse controlled by electronics in the ultrasonic imaging system.

An ultrasonic imaging apparatus having improved field of view for improved volumetric imaging is hereinafter disclosed. In particular, the apparatus includes an ultrasonic probe and a plurality of acoustic elements configured and arranged to form a two-dimensional array. The two-dimensional array is further configured and adapted to fit within the housing and each of the acoustic elements is capable of generating an acoustic pulse and/or receiving an echo signal. Further included in the apparatus is a beam controller coupled to the two-dimensional array and capable of driving at least one of the acoustic elements, thereby producing an acoustic pulse for impinging an acoustic target, and preferably activating a plurality of acoustic elements to form an acoustic beam. The acoustic target reflects at least a portion of the acoustic beam as at least one echo signal. The beam controller further includes associated circuitry capable of controlling directional movement of the acoustic beam. A signal processor is coupled to the two-dimensional array for processing at least one echo signal to form at least one image signal. A display operatively coupled to the signal processor is further included for displaying data corresponding to the at least one image signal.

Additionally, a method for improving the field of view, thereby improving the volumetric imaging in an ultrasonic imaging apparatus is hereinafter disclosed. The method includes providing an ultrasonic probe having a plurality of acoustic elements configured and arranged to form a two-dimensional array that is configured and adapted to fit within the ultrasonic probe. Each of the acoustic elements is capable of generating an acoustic pulse and/or receiving an echo signal. A beam controller coupled to said two-dimensional array is provided where the beam controller is capable of driving at least one of the acoustic elements to produce the acoustic pulse for impinging an acoustic target to generate at least one echo signal. Preferably, the beam controller activates a plurality of acoustic elements to form an acoustic beam. Further still, the beam controller has associated circuitry capable of controlling directional movement of the acoustic beam, and a signal processor coupled to the two-dimensional array for processing at least one echo signal, thereby forming at least one image signal. The ultrasonic imaging system processes at least one echo signal to form at least one image signal and is capable of displaying data corresponding to the at least one image signal on a display.

Further disclosed is an ultrasonic imaging kit that includes at least two ultrasonic probes configured and dimensioned for alternative placement within the ultrasonic imaging system. Each ultrasonic probe includes a transducer assembly with an interface for communicating with circuitry of the ultrasonic probe. Each transducer assembly further includes a plurality of acoustic elements configured and arranged to form a two-dimensional array and the two-dimensional array is configured and adapted to fit within the ultrasonic probe. It is preferred that at least two ultrasonic probes are provided where at least one of the ultrasonic probes has a different transducer assembly from at least one other ultrasonic probe. Each of the acoustic elements is capable of generating an acoustic pulse and/or receiving an echo signal. The beam controller is coupled to the two-dimensional array and is capable of driving at least one of the acoustic elements to produce the acoustic pulse for impinging an acoustic target and generating at least one echo signal, and preferably driving a plurality of acoustic elements to form an acoustic beam. The beam controller has associated circuitry capable of controlling directional movement of the acoustic beam and a signal processor coupled to the two-dimensional array for processing at least one echo signal, thereby forming at least one image signal. The display is capable of displaying data representing the at least one image signal.

An ultrasonic imaging system having improved field of view for improved volumetric imaging is hereinafter disclosed and includes an ultrasonic probe, a plurality of acoustic elements configured and arranged to form a two-dimensional array that is configured and adapted to fit within the ultrasonic probe. Each of the acoustic elements is capable of generating an acoustic pulse and/or receiving an echo signal. Coupled to the two-dimensional array is a beam controller that is capable of driving at least one of the acoustic elements to produce the acoustic pulse for impinging an acoustic target, thereby generating at least one echo signal. The beam controller has associated circuitry capable of controlling directional movement of the acoustic pulse is operatively coupled to the transmitter and communicates with a signal processor coupled to said two-dimensional array for processing at least one echo signal, thereby forming at least one image signal where the display is capable of displaying data corresponding to the at least one image signal. A means for connecting the housing to an ultrasonic imaging apparatus is further included.

The foregoing objects and advantages of the present invention may be more readily understood by one skilled in the art with reference being had to the following detailed description of preferred embodiments thereof, taken in conjunction with the accompanying drawings in which.

Several embodiments of the present invention are hereby disclosed in the accompanying description in conjunction with the figures. Preferred embodiments of the present invention will now be described in detail with reference to the figures wherein like reference numerals identify similar or identical elements. As used herein, the term "distal" refers to that portion of the tool, or component thereof which is further from the user while the term "proximal" refers to that portion of the tool or component thereof which is closer to the user.

Figure 1:
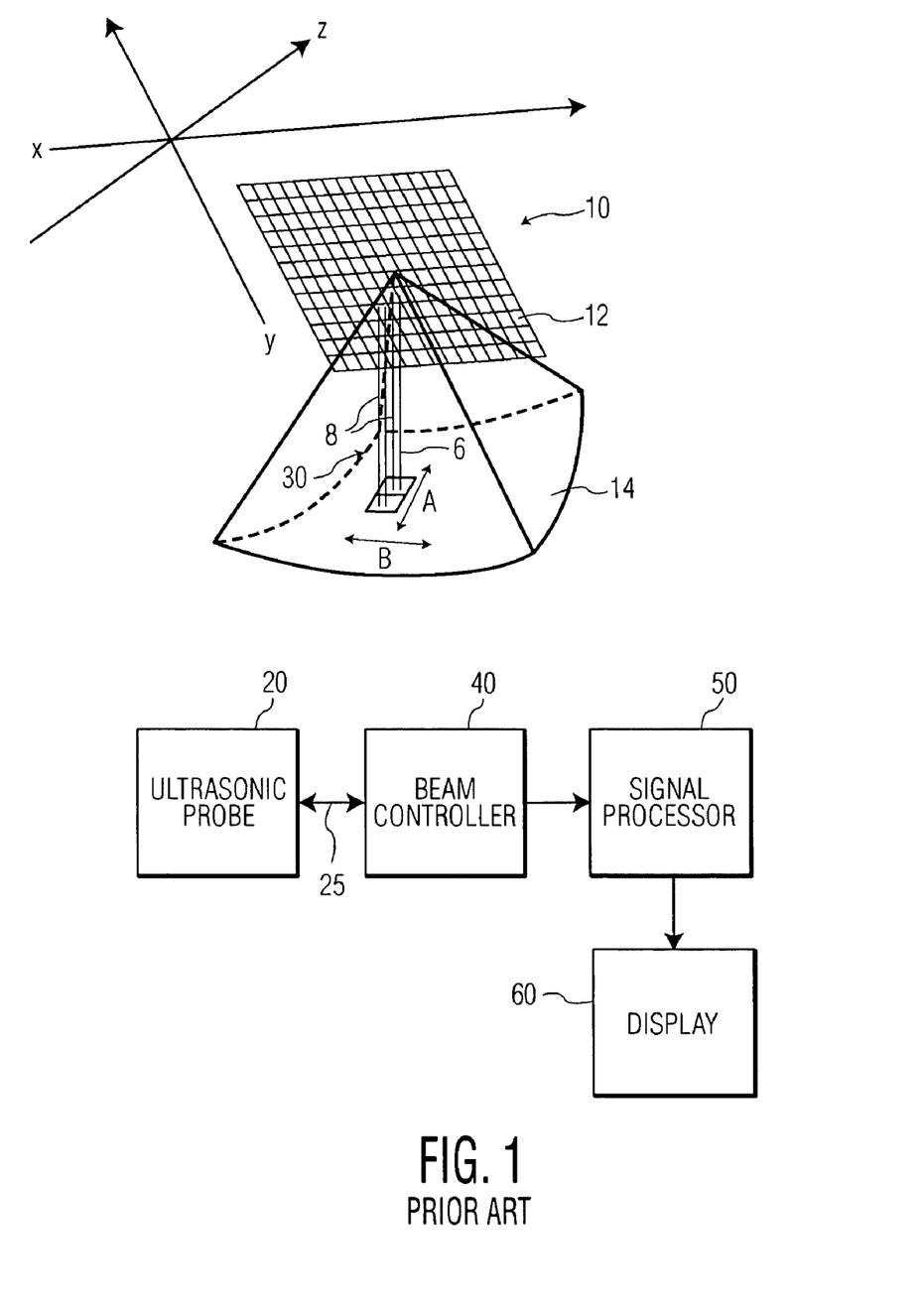
FIG. 1 is an ultrasonic imaging system with a prior art two-dimensional array having acoustic beam steering.

An example of an ultrasonic imaging system using a conventional ultrasonic transducer array is illustrated in FIG. 1. An ultrasonic probe 20 includes a conventional two-dimensional ultrasonic transducer array 10 (see FIG. 1) with a plurality of acoustic elements 12 arranged in a number of columns and rows. These acoustic elements 12 are configured and arranged in a generally planar configuration. Each acoustic element 12 is formed from a suitable piezoelectric material and is capable of generating an acoustic pulse 8 at a particular frequency when a driver signal is applied to the acoustic element 12. The generated acoustic pulse 8 impinges on an acoustic target where at least some of the energy in the acoustic pulse 8 is reflected back towards the acoustic element 12 as an echo signal 6. In addition, each acoustic element 12 is capable of receiving the echo signal 6 from the acoustic target and generating a corresponding output signal. Conventional ultrasonic imaging systems have a beam controller 40 for generating the driver signal 25 and for electronically steering the acoustic pulse 8 ("beam steering").

Two-dimensional transducer arrays 10 are generally employed with accompanying circuitry to produce three-dimensional ultrasonic images of the acoustic target since the acoustic beam 30 is generated by acoustic elements 12 in both the rows and the columns of the two-dimensional transducer array 10. By controlling the phase differential, or the time delay, among the acoustic elements 12 that are driven by the beam controller 40 (i.e. phase-shifting), a number of acoustic pulses 8 are combined into an acoustic beam 30, that can be electronically steered by the beam controller 40 in both directions A and B (represented by double-ended arrows A and B in FIG. 1) to acquire acoustic targets within the field of view of the ultrasonic transducer array 10 (i.e. "beam steering"). However, conventional two-dimensional ultrasonic transducer arrays 10 have limited fields of view along with a relatively small acquired volume 14 that is close the surface of the ultrasonic transducer array 10, shown as the acquired volume 14 in FIG. 1. In addition, ultrasonic imaging systems further include a signal processor 50 and a display 60.

Figure 2:
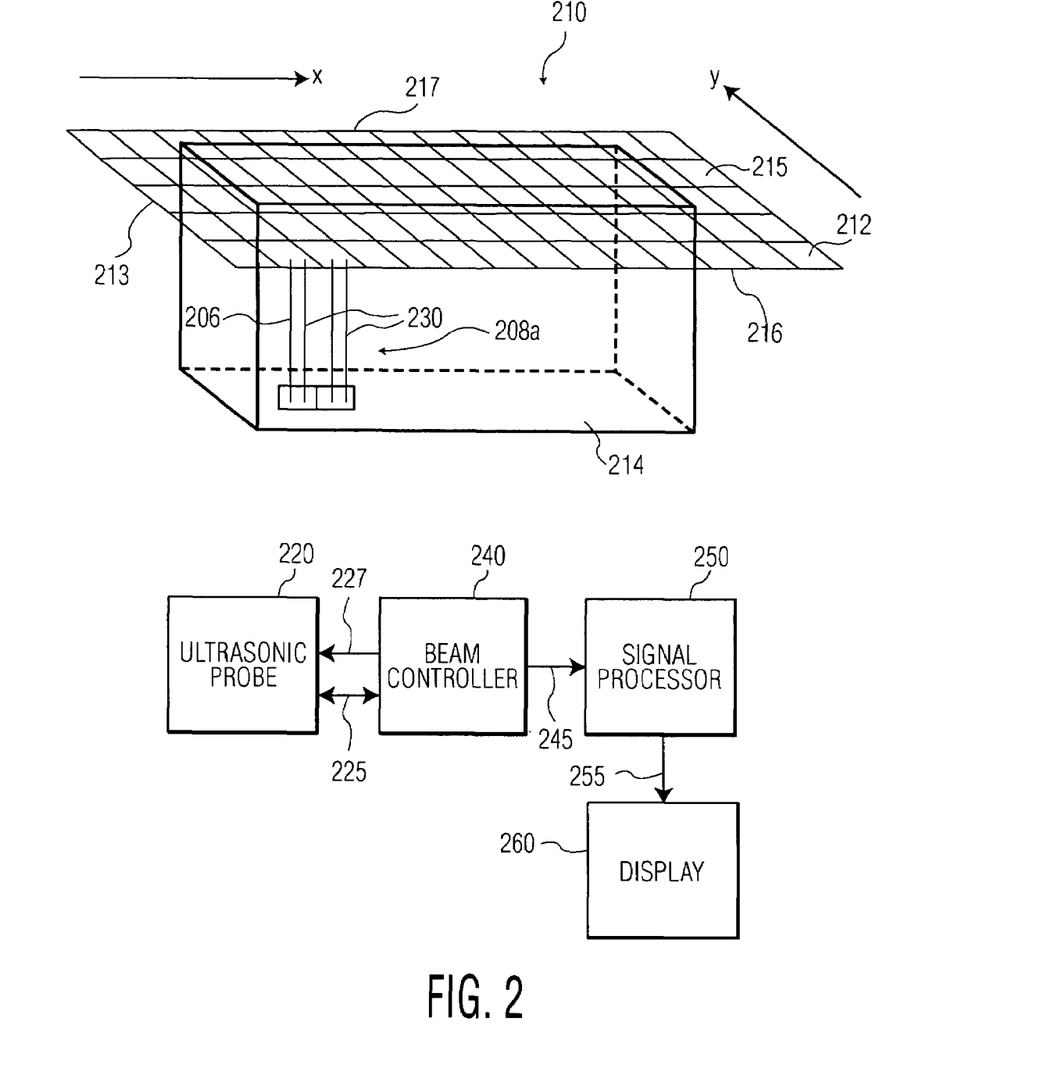
FIG. 2 is an ultrasonic imaging system with a two-dimensional array including acoustic beam tractor treading according to an embodiment of the present disclosure.
Figure 2A:
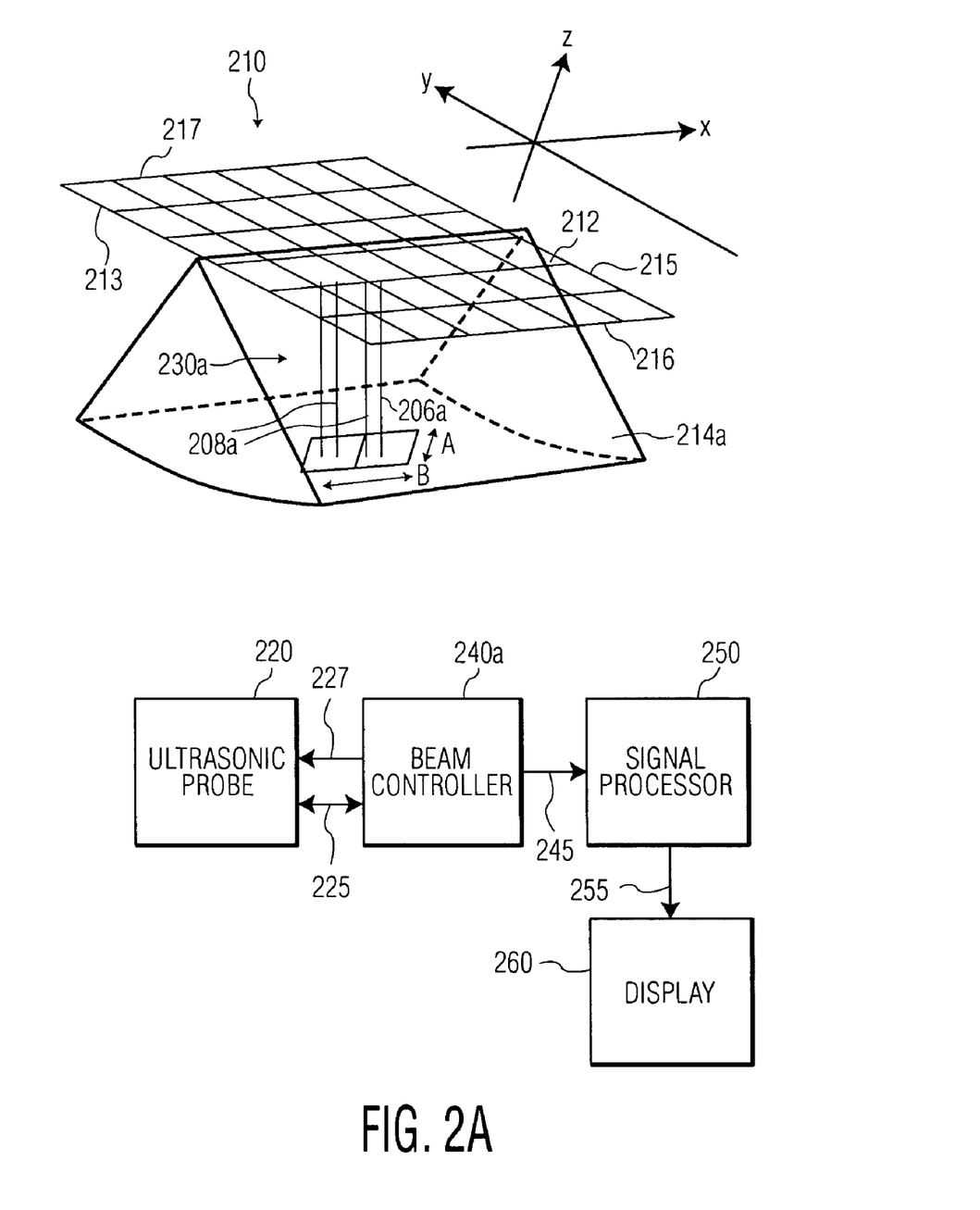
FIG. 2a is an ultrasonic imaging system with a two-dimensional array having acoustic beam steering and beam tractor treading according to an embodiment of the present disclosure.

Ultrasonic imaging systems according to an embodiment of the present invention are shown in FIGS. 2 and 2a, and further described with specificity hereinafter. Referring first to FIG. 2, the ultrasonic imaging system includes an ultrasonic probe 220 with a two-dimensional transducer array 210, a beam controller 240, a signal processor 250, and a display 260. A plurality of acoustic elements 212 is disposed in a number of rows and columns to form the two-dimensional transducer array 210. In the presently disclosed two-dimensional transducer array 210, the acoustic pulses 208 are generated by acoustic elements 212 in the two-dimensional transducer array 210 to form an acoustic beam 230. The beam controller 240 is coupled by a connecting means 225 to the acoustic elements 212 of the two-dimensional transducer array 210 and generates a driver signal 227 that is communicated to one or more of the acoustic elements 212. Each of the acoustic elements 212 is formed from a suitable piezoelectric material and is capable of generating an acoustic pulse 208 and receiving an echo signal 206. It is contemplated that a number of the acoustic elements 212 may be "passive" elements (i.e. not configured for generating acoustic pulses or receiving echo signals) while the remaining acoustic elements 212 are "active" elements (i.e. configured for generating an acoustic pulse 208 and receiving an echo 206).

The connecting means 225 is generally a cable including a plurality of conducting elements, such as wires. Alternatively, the connecting means 225 can be significantly improved if some of the electronics are located in the ultrasonic probe housing and the connecting means is a wireless connection, such as infrared or radio frequency.

The beam controller 240 is operatively coupled to the two-dimensional transducer array 210 for varying characteristics and properties of the generated acoustic pulses 208. The beam controller 240 is capable of generating a plurality of driver signals 227 that correspond to the number of acoustic elements 212 to be activated. The beam controller 240 further controls the timing of the respective driver signals 227 applied to the acoustic elements 212 (i.e. phase shifting), and the resulting acoustic beam 230 is initially generated at a first end 213 of the two-dimensional transducer array 210 and advances along a longitudinal axis-X of the two-dimensional transducer array 210 towards a second end 215.

More specifically, when the acoustic beam 230 is initially formed, a number of the active acoustic elements 212 disposed in the first column that is adjacent the first end 213 are actuated by corresponding driver signals 227 from the beam controller 240 simultaneously. After the acoustic elements 212 of the column are activated by the corresponding driver signals 227, the process repeats itself in the next adjacent column of acoustic elements 212. Activation of the acoustic elements 212 in this manner is referred to as beam tractor treading and is used to generate an acquired three-dimensional volume 214 as shown in FIG. 2. It is further contemplated that more than one column of acoustic elements 212 may be activated by the beam controller 240 simultaneously thereby forming an active aperture including the acoustic beam 230. Advantageously, the beam controller 240 advances the active aperture by a predetermined number of columns to acquire the desired volume.

Alternatively, the beam controller 240 can actuate a number of active acoustic elements 212 in a number of columns where the number of acoustic elements 212 activated is less than the number of active acoustic elements 212 in each of the columns thereby forming a smaller active aperture and acoustic beam 230. Preferably, the beam controller 240 causes the generation of acoustic beam 230 within the active aperture and the beam controller 240 is adapted to move the active aperture and the acoustic beam 230 along the row of acoustic elements 212. After the active aperture reaches the end of the row of acoustic elements 212 at back end portion 217 of the transducer array 210, the beam controller 240 shifts the acoustic beam 230 and the active aperture by the number of previously activated columns and causes the active aperture to advance towards a front end portion 216 of the transducer array 210. By advantageously controlling the motion and direction of the acoustic beam 230 and resultant active aperture, a three-dimensional volume is obtainable.

The acoustic pulses 208 are directed towards an acoustic target and portions of the acoustic pulses 208 are reflected towards the two-dimensional transducer array 210 as echo signals 206. After each acoustic element 212 activates to generate the acoustic pulse 208, the acoustic element 212 is capable of receiving the echo signal 206. This echo signal 206 contains information relating to the acoustic target and generates an output signal 245 from the acoustic element. This output signal 245 is communicated through the transmitter 230 and the pulse controller 240 to the signal processor 250. In the signal processor 250, the output signal 245 of the acoustic element 212 is transformed by associated circuitry in the signal processor 250 to generate an image signal 255. A display 260 is operatively coupled to the output of the signal processor 250 for receiving one or more image signals 255 and for transforming the image signals 255 into a video image. Essentially, the display 260 is capable of displaying data corresponding to the at least one image signal 255. It is preferred that the display 260 be a video monitor that is readily viewable by attending personnel.

Turning now to FIG. 2a, the same or similar components of the previously disclosed embodiment are included in the ultrasonic imaging system. However, in this embodiment, the acoustic pulse 208a combines the ultrasonic imaging system of FIG. 2 with beam tractor treading as discussed hereinabove with beam steering. Beam steering, as previously discussed, occurs when the combination of the transmitter generated driver signals 225 are coupled and controlled by the beam controller 240a, using phase shifting, to generate the acoustic pulses 208a from the activate acoustic elements 212 thereby forming an acoustic beam 230a. By advantageously combining beam tractor treading and beam steering, a three-dimensional volume 214a (see FIG. 2a) having a greater field of view, and therefore a greater volumetric image, is obtainable.

In this embodiment of the present invention, beam tractor treading generates an acoustic beam 230a starting with the acoustic elements 212 disposed in the column adjacent to a first side 213 of the two-dimensional transducer array 210. As before, the transmitter 230 in cooperation with the beam controller 240a causes the active acoustic elements 212 to be activated simultaneously in each column to generate the acoustic beam 230a. After all the acoustic elements 212 in the column are activated, the next adjacent column of acoustic elements 212 is activated. As before, the columns of acoustic elements 212 are activated in sequence and controllable by the beam controller 240a In addition, the beam controller 240a phase-shifts the generation of the acoustic pulses 208a of the activated acoustic elements 212 for "beam steering." By advantageously advancing (i.e. beam tractor treading) the phase-shifting of the acoustic beam 230a (i.e. beam steering), the two-dimensional transducer array 210 of the present invention is capable of capturing and displaying the three-dimensional acquired volume image 214a as seen in FIG. 2a. It is further contemplated that more than one column of acoustic elements 212 may be activated to form the acoustic beam 230a.

Figure 3:
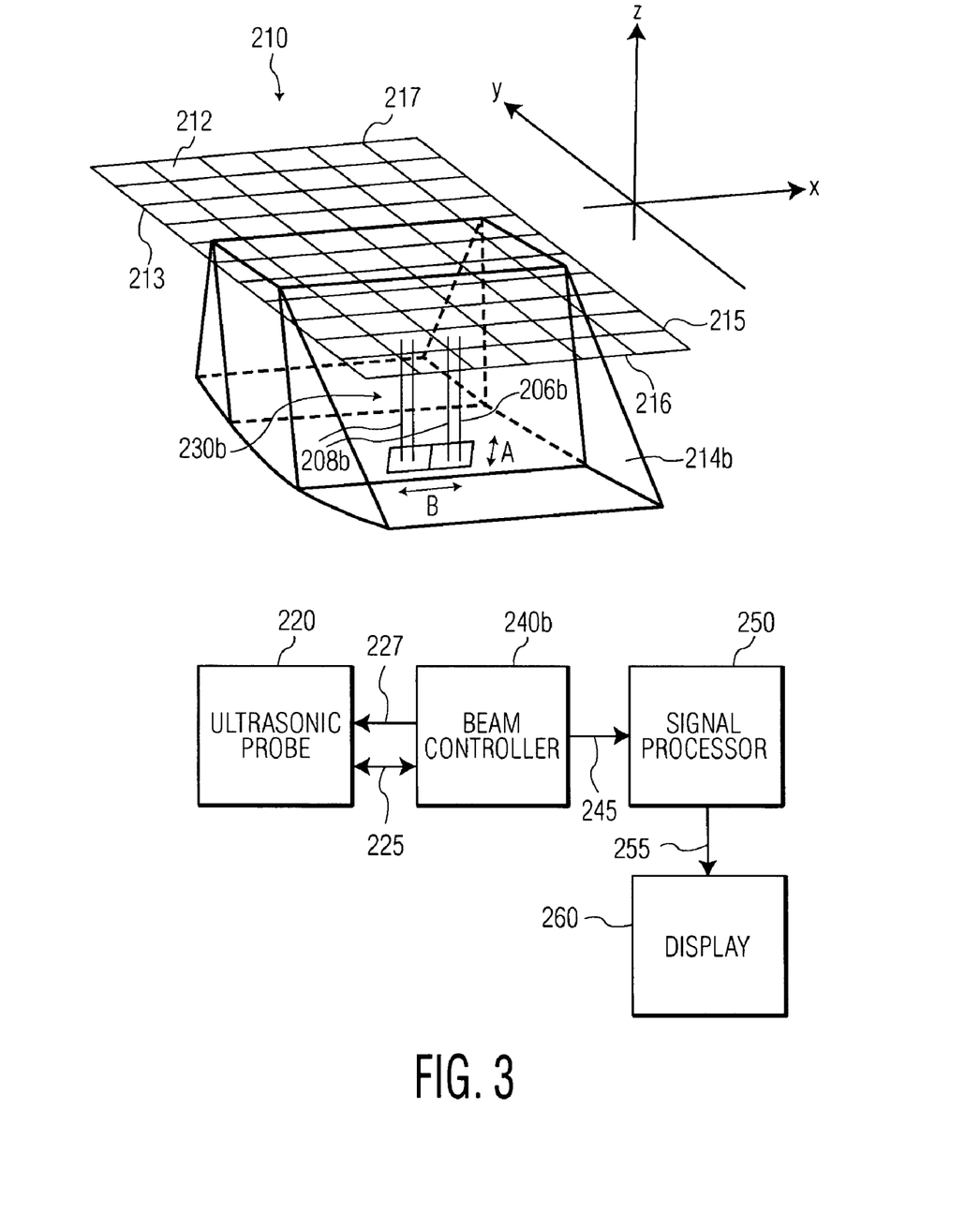
FIG. 3 is an ultrasonic imaging system with a two-dimensional array having a combination of acoustic beam steering and acoustic beam tractor treading according to another embodiment of the present disclosure.

Another exemplary embodiment of the present invention is illustrated in FIG. 3. In this embodiment, an ultrasonic imaging system includes an ultrasonic probe 220 with a two-dimensional ultrasonic array 210, a beam controller 240b, a signal processor 250, and a display 260. Similar to the embodiments of FIGS. 2 and 2a, the two-dimensional transducer array 210 is a generally planar arrangement of acoustic elements 212 where the plurality of acoustic elements 212 is configured and arranged in a number of rows and columns. It is contemplated that within the transducer array 210, the number of acoustic elements may include a quantity of passive acoustic elements 212 disposed among the active acoustic elements 212 (i.e. a sparse array).

Similar to the previous embodiment, the acoustic pulse 208b is directed towards an acoustic target and a portion of the acoustic pulse 208b is reflected towards the two-dimensional transducer array 210 as an echo signal 206b. After each acoustic element 212 activates to generate the acoustic pulse 208b, the acoustic element 212 is capable of receiving the echo signal 206b. This echo signal 206b contains information relating to the acoustic target and generates an output signal 245 from the acoustic element 212. This output signal 245 is communicated through the transmitter 230 and the beam controller 240b to the signal processor 250. In the signal processor 250, the output signal 245 of the acoustic element 212 is transformed by associated circuitry in the signal processor 250 to generate an image signal 255. A display 260 is operatively coupled to the output of the signal processor 250 for receiving one or more image signals 255 and for transforming the image signals 255 into a video image. Essentially, the display 260 is capable of displaying data corresponding to the at least one image signal 255. It is preferred that the display 260 be a video monitor that is readily viewable by attending personnel.

Coupled to the two-dimensional transducer array 210 is the beam controller 240 using a connecting means 225. Generally, the connecting means 225 is a cable having a plurality of conducting elements, such as wires. Alternatively, the connecting means 225 can be a wireless connection, such as infrared or radio frequency. In operation, the beam controller generates a plurality of driver signals 227 that correspond to the number of acoustic elements 212 to be activated. As previously discussed, each acoustic element 212 is capable of generating an acoustic pulse 208b or receiving an echo signal 206b. The beam controller 240 controls the generation of the respective driver signals 227. In this embodiment, a first column of acoustic elements 212 is disposed adjacent to a first end 213 of the two-dimensional transducer array 210.

Advantageously, the beam controller 240b generates a number of driver signals 227 that activate the active acoustic elements 212 in each column in a sequential manner. Activating acoustic elements 212 in each column sequentially, before activating the next adjacent column permits beam tractor treading along a longitudinal axis-X of the two-dimensional transducer array 210 and a lateral axis-Y of the two-dimensional transducer array 210. Further still, the beam controller 240b, causes the generated acoustic pulses 206b to be phase-shifted thereby generating an acoustic beam 230b by "beam steering." By advantageously combining beam steering of the acoustic beam 230b with tractor treading in both the longitudinal and lateral directions (i.e. rasterizing), the ultrasonic imaging system is capable of capturing and displaying an acquired volume image 214b as illustrated in FIG. 3. It is envisioned that the transducer array 210 includes acoustic elements 212 that may include a quantity of passive acoustic elements 212 disposed among the active acoustic elements 212 (i.e. a sparse array).

Figure 4:
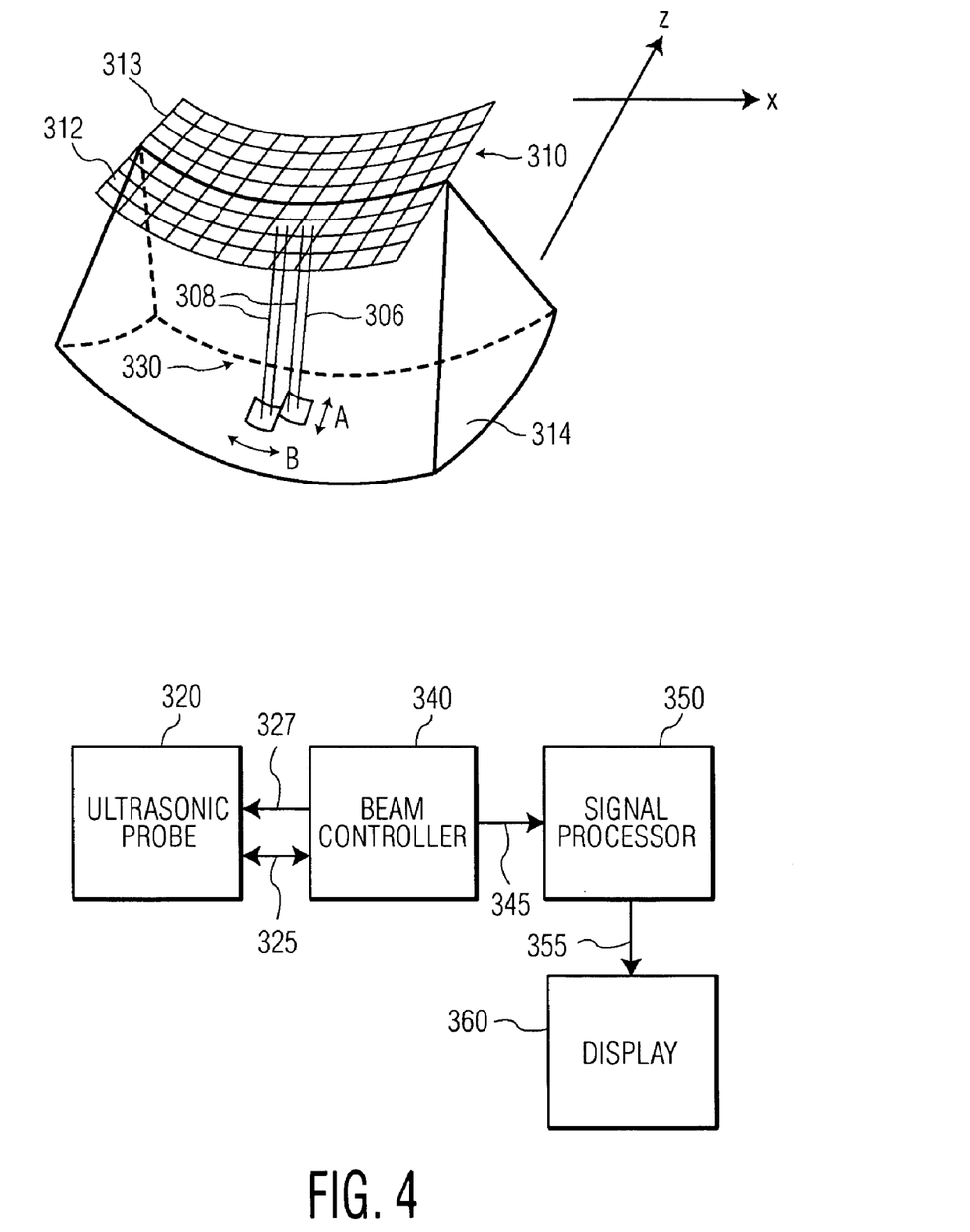
FIG. 4 is an ultrasonic imaging system with a cylindrical two-dimensional array having acoustic beam steering and acoustic tractor treading according to a further embodiment of the present disclosure.

In an alternative embodiment, an ultrasonic imaging system is shown in FIG. 4 and includes an ultrasonic probe 320 having a two-dimensional transducer array 310. The transducer array 310 includes a plurality of acoustic elements 312 generally arranged in a cylindrical configuration. As in previous embodiments, each acoustic element 312 is formed from a suitable piezoelectric material having the capability to generate an acoustic pulse 308 in response to an input driver signal 327 and to receive echo signals 306 from an acoustic target to generate an output signal 345. The ultrasonic imaging system further includes a beam controller 340, a signal processor 350, and a display 360. The beam controller 340 is coupled to the two-dimensional transducer array 310 by a connecting means 325 and is capable of generating a number of driver signals 327 that correspond to the number of active acoustic elements 312. The connecting means 325 is generally a cable including a plurality of connecting elements, such as wires. Alternatively, the connecting means 325 can be a wireless connection, such as infrared or radio frequency. Further still, the beam controller is capable of communicating the generated output signals 345 from the acoustic elements 312 to the signal processor 350.

Cooperatively coupled to the ultrasonic probe 320 is a beam controller 340 for phase shifting the driver signals 327 that generate the acoustic pulses 308 and communicating the output signals 345 to the signal processor 350. Advantageously, the beam controller 340 generates a number of acoustic pulses 308 to form an acoustic beam 330 by simultaneously activating the active acoustic elements 312 in each column. Operationally, a first column of acoustic elements 312 is adjacent to a first end 313 of the cylindrical two-dimensional transducer array 310 where the acoustic elements 312 disposed in the column are activated simultaneously. In a preferred embodiment, as the acoustic elements 312 are activated, the resulting acoustic beam 330 is phase-shifted by the beam controller 340 (i.e. beam steering). After the first column has been activated, the beam controller 340 activates the next adjacent column of acoustic elements 312 to advance the acoustic beam 330 along the longitudinal axis-X of the cylindrical two-dimensional transducer array 310. By combining longitudinal tractor treading and beam steering, the ultrasonic imaging system is capable of capturing and displaying an acquired volume image 314 as seen in FIG. 4. It is contemplated that multiple columns of acoustic elements 312 may be activated by the beam controller 340 to produce a larger acoustic beam 330 and therefore, a larger active aperture for capturing a larger volume image.

As in the previous embodiments, the acoustic pulses 308 are directed towards an acoustic target and portions of the acoustic pulses 308 is reflected towards the two-dimensional transducer array 310 as echo signals 306. After each acoustic element 312 activates to generate the acoustic pulse 308, the acoustic element 312 is capable of receiving the echo signal 306. This echo signal 306 contains information relating to the acoustic target and generates an output signal 345 from the acoustic element 312. This output signal 345 is communicated through the transmitter 330 and the beam controller 340 to the signal processor 350. In the signal processor 350, the output signal 345 of the acoustic element 312 is transformed by associated circuitry in the signal processor 350 to generate an image signal 355. A display 360 is operatively coupled to the output of the signal processor 350 for receiving one or more image signals 355 and for transforming the image signals 355 into a video image. Essentially, the display 360 is capable of displaying data corresponding to the at least one image signal 355. It is preferred that the display 360 be a video monitor that is readily viewable by attending personnel. It is contemplated that within the transducer array 310, the number of acoustic elements may include a quantity of passive acoustic elements 312 disposed among the active acoustic elements 312 (i.e. a sparse array).

Figure 5:
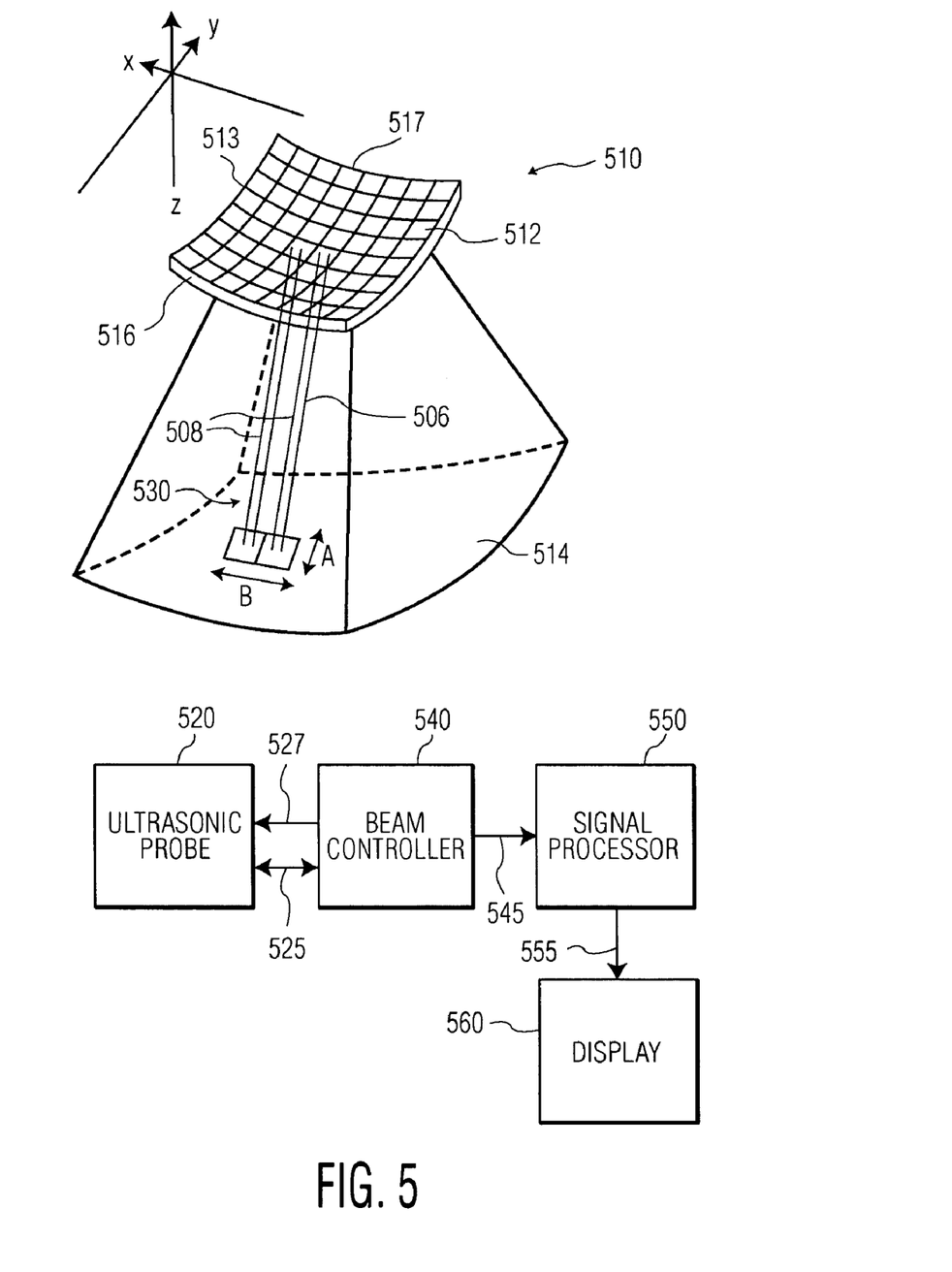
FIG. 5 is an ultrasonic imaging system with a convex two-dimensional array having acoustic tractor treading according to a further embodiment of the present disclosure.

In a further embodiment, an ultrasonic imaging system is illustrated in FIG. 5 and includes an ultrasonic probe 520 with a two-dimensional transducer array 510 having a generally convex configuration. A plurality of acoustic elements 512 is disposed in a number of rows and columns. Preferably, the two-dimensional transducer array 510 will have substantially equal longitudinal and lateral dimensions. Additionally, the ultrasonic imaging system includes a beam controller 540, a signal processor 550, and a display 560. The beam controller 540 is operatively coupled to the convex two-dimensional transducer array 510 and communicates a number of driver signals 527 that correspond to the number of acoustic elements 512 to be activated. A connecting means 525 operatively couples the beam controller 540 to the convex two-dimensional transducer array. Typically, the connecting means 525 is a cable having a plurality of conducting elements, such as wires. Alternatively, the connecting means 525 can be a wireless connection, such as infrared or radio frequency.

Similar to the previous embodiments, the acoustic pulse 508 is directed towards an acoustic target and a portion of the acoustic pulse 508 is reflected towards the two-dimensional transducer array 510 as an echo signal 506. After each acoustic element 512 activates to generate the acoustic pulse 508, the acoustic element 512 is capable of receiving the echo signal 506. This echo signal 506 contains information relating to the acoustic target and generates an output signal 545 from the acoustic element 512. This output signal 545 is communicated through the transmitter 530 and the beam controller 540 to the signal processor 550. In the signal processor 550, the output signal 545 of the acoustic element 512 is transformed by associated circuitry in the signal processor 550 to generate an image signal 555. A display 560 is operatively coupled to the output of the signal processor 550 for receiving one or more image signals 555 and for transforming the image signals 555 into a video image. Essentially, the display 560 is capable of displaying data corresponding to the at least one image signal 555. It is preferred that the display 560 be a video monitor that is readily viewable by attending personnel.

It is preferred that the beam controller 540 is cooperatively coupled to the beam ultrasonic probe 520 for activating the acoustic pulses 508. In operation, the output of the beam controller 540 activates a plurality of active acoustic elements 512. Initially, the acoustic elements 512 in a first column, that is adjacent to a first end 513 of the convex two-dimensional transducer array 510, are activated by the driver signals 527 from the beam controller 540. The first acoustic element 512 that is activated is the one disposed in the corner between the first end 513 and a first side 516 of the convex two-dimensional transducer array 510. The remaining acoustic elements 512 located in the first column are activated sequentially to generate the acoustic beam 530 and advance the acoustic beam 530 along a lateral axis-Y. After the last acoustic element 512 in the first column is activated, the acoustic element 512 disposed in the next adjacent column at a second side 517 of the convex two-dimensional transducer array 510 is activated. The acoustic elements 512 in this column are activated sequentially to advance the acoustic beam 530 towards the first side 516. The process is repeated for the remaining columns in the convex two-dimensional transducer array 510 and advancing the acoustic beam 530 one or more columns at a time (i.e. tractor treading) along a longitudinal axis-X. Further still, the beam controller 540 advantageously phase-shifts the acoustic pulses 508 during the formation of the acoustic beam 530 (i.e. "beam steering"). By advantageously combing beam tractor treading and beam steering with a convex two-dimensional transducer array 510, the ultrasonic imaging system is capable of capturing and displaying the volume image 514 illustrated in FIG. 5. It is contemplated that within the transducer array 510, the number of acoustic elements may include a quantity of passive acoustic elements 512 disposed among the active acoustic elements 512 (i.e. a sparse array).

Hereinafter disclosed is a method for improving volumetric imaging in an ultrasonic imaging apparatus. According to an embodiment of the present invention, an ultrasonic probe is provided that includes a plurality of acoustic elements, a number of which are active acoustic elements, that are disposed in a number of columns and rows to form a two-dimensional transducer array. Advantageously, the two-dimensional transducer array is configured and adapted according to one of the previously disclosed embodiments. Further provided is a beam controller that is operatively coupled via a connecting means to the two-dimensional transducer array where the beam controller is capable of driving at least one of the active acoustic elements by generating driver signals that generate a corresponding number of acoustic pulses, thereby forming an acoustic beam. Typically, the connecting means is a cable including a plurality of conducting elements, such as wires. Alternatively, the connecting means can be a wireless connection, such as infrared or radio frequency.

The acoustic beam impinges on an acoustic target and generates at least one echo signal in response. Operatively coupled to the transducer array is the beam controller with associated circuitry for controlling the respective driver signals. As discussed hereinabove, the beam controller phase shifts the driver signals to actuate respective acoustic elements for controlling the generated acoustic beam. The beam controller is capable of generating driver signals for beam steering and beam tractor treading, thereby increasing the field of view for improving the volumetric imaging capabilities of the two-dimensional transducer array. The echo signals that are reflected from the acoustic target are coupled through the beam controller to an input of a signal processor. These echo signals are transformed by the signal processor into image signals where the display is capable of displaying data corresponding to the image signals.

In an exemplary method of use, an operator positions the ultrasonic probe including the two-dimensional transducer array in a region to be imaged. After the ultrasonic probe is positioned, the operator actuates the beam controller to generate the desired driver signals for actuating the acoustic elements, thereby generating the acoustic beam. Additionally, the beam controller causes the acoustic beam to advance in a desired direction of movement (i.e. beam tractor treading) and/or phase shifting the acoustic pulses (i.e. beam steering). Advantageously, the actuation of the beam controller combines the generation and motion of the acoustic beam. After the acoustic beam impinges on the acoustic target, echo signals are reflected towards the two-dimensional transducer array for capture by the acoustic elements. These echo signals are coupled through the beam controller to the signal processor to generate the image signal. A display receives the image signal and displays data corresponding to the image signal as a viewable image to the operator.

Additionally, a kit for improving the field of view and the volumetric imaging in an ultrasonic imaging system is herein disclosed. In a preferred embodiment, the ultrasonic imaging kit includes at least two ultrasonic probes having associated circuitry where each ultrasonic probe is configured and adapted to receive an ultrasonic imaging assembly. Each ultrasonic probe includes an ultrasonic transducer assembly having interfaces for interfacing with the associated circuitry of the ultrasonic probe. In a minimum configuration, at least one of the ultrasonic transducer assemblies includes a plurality of acoustic elements configured and arranged to form a two-dimensional transducer array. As in previous embodiments, each acoustic element is capable of producing an acoustic pulse in response to an inputted driver signal and receiving an echo signal from an acoustic target.

Coupled via a connecting means to the transducer assembly is a beam controller. Generally, the connecting means is a cable having a plurality of connecting elements, such as wires. Alternatively, the connecting means can be a wireless connection, such as infrared or radio frequency. The beam controller is capable of generating a plurality of driver signals corresponding to the number of acoustic elements to be actuated. Preferably, the beam controller is capable of adjusting the driver signals, thereby controlling the generation, phase shifting (i.e. beam steering), and motion (i.e. beam tractor treading) of the acoustic beam. A signal processor for receiving the echo signals and forming corresponding image signals is further included and is coupled to a display. The display is capable of displaying data corresponding to the image signals generated by the signal processor as a viewable image.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

The invention claimed is:

1. An ultrasonic imaging apparatus comprising:
an ultrasonic probe;
a plurality of acoustic elements configured and arranged to form a two-dimensional array, said two-dimensional array configured and adapted to fit within the ultrasonic probe wherein said plurality of acoustic elements includes at least two active acoustic elements capable of generating acoustic pulses and/or receiving echo signals; and
a beam controller coupled to said two-dimensional array, said beam controller capable of driving the at least two active acoustic elements to produce said acoustic pulses originating from the two active acoustic elements for impinging an acoustic target to generate the echo signals, and having associated circuitry configured for controlling directional movement of said acoustic pulses by a combination of tractor treading and beam steering.

2. The ultrasonic imaging apparatus of claim 1, further including a signal processor coupled to said two-dimensional array for processing the echo signal, thereby forming at least one image signal.

3. The ultrasonic imaging apparatus of claim 1, wherein said two-dimensional array is configured and arranged in a substantially planar configuration.

4. The ultrasonic imaging apparatus of claim 1, wherein said two-dimensional array is configured and arranged in a substantially cylindrical configuration.

5. The ultrasonic imaging apparatus of claim 1, wherein said two-dimensional array is configured and arranged in a substantially convex configuration.

6. The ultrasonic imaging apparatus of claim 5, wherein said convex configuration includes substantially equal lateral and longitudinal dimensions.

7. A method for improving volumetric imaging in an ultrasonic imaging apparatus comprising the acts of:
providing an ultrasonic probe;
providing a plurality of acoustic elements configured and arranged to form a two-dimensional array, said two-dimensional array configured and adapted to fit within the ultrasonic probe wherein said plurality of acoustic elements includes at least two active acoustic element capable of generating an acoustic pulse originating from the two active acoustic elements and/or receiving echo signal;
providing a beam controller coupled to said two-dimensional array, said beam controller capable of driving the at least two of active acoustic element to produce said acoustic pulse for impinging an acoustic target to generate the echo signals and having associated circuitry configured for controlling directional movement of said acoustic pulses by a combination of tractor treading and beam steering; and
actuating said beam controller to generate and move said acoustic pulse.

8. The method of claim 7, further comprising the act of providing a signal processor coupled to said two-dimensional array for processing the echo signals, thereby forming at least one image signal.

9. The method of claim 8, further comprising the act of displaying data corresponding to the at least one image signal.

10. The method of claim 7, wherein said two-dimensional array is configured and arranged in a substantially planar configuration.

11. The method of claim 7, wherein said two-dimensional array is configured and arranged in a substantially cylindrical configuration.

12. The method of claim 7, wherein said two-dimensional array is configured and arranged in a substantially convex configuration.

13. The method of claim 12, wherein said convex configuration includes substantially equal lateral and longitudinal dimensions.

14. An ultrasonic imaging kit comprising:
at least two ultrasonic probes, each having a transducer array and associated circuitry where each ultrasonic probe is configured and dimensioned for alternative placement within an ultrasonic system, at least one of a first ultrasonic probe further including a plurality of acoustic elements configured and arranged to form a two-dimensional array, said two-dimensional array configured and adapted to fit within the ultrasonic probe wherein said plurality of acoustic elements includes at least two active acoustic elements capable of generating an acoustic pulse and/or receiving echo signal; and
a beam controller coupled to the circuitry of the first ultrasonic probe and in communication with said transducer array disposed within said ultrasonic probe, said beam controller capable configured for driving the at least two active acoustic elements to produce said acoustic pulses originating from the two active acoustic for impinging an acoustic target to generate echo signals and having associated circuitry configured for controlling directional movement of said acoustic pulses by a combination of tractor treading and beam steering.

15. The ultrasonic imaging kit of claim 14, further including a signal processor coupled to said two-dimensional array for processing the echo signals, thereby forming at least one image signal.

16. The ultrasonic imaging kit of claim 14, wherein said two-dimensional array is configured and arranged in a substantially planar configuration.

17. The ultrasonic imaging kit of claim 14, wherein said two-dimensional array is configured and arranged in a substantially cylindrical configuration.

18. The ultrasonic imaging kit of claim 14, wherein said two-dimensional array is configured and arranged in a substantially convex configuration.

19. The ultrasonic imaging kit of claim 18, wherein said convex configuration includes substantially equal lateral and longitudinal dimensions.

20. An ultrasonic imaging system comprising:
an ultrasonic probe;
a plurality of acoustic elements configured and arranged to form a two-dimensional array, said two-dimensional array configured and adapted to fit within the ultrasonic probe wherein said plurality of acoustic elements includes at least two active acoustic elements capable of generating an acoustic pulse and/or receiving an echo signals; and
a beam controller coupled to said two-dimensional array, said beam controller configured for driving the at least two active acoustic element to produce said acoustic pulses originating from the two active acoustic for impinging an acoustic target to generate at the echo signal, and having associated circuitry configured for controlling directional movement of said acoustic pulse by a combination of tractor treading and beam steering.

21. The ultrasonic imaging system of claim 20, further comprising:
a signal processor coupled to said two-dimensional array for processing the echo signals, thereby forming at least one image signal;
means for connecting said ultrasonic probe to an ultrasonic imaging apparatus; and
means for displaying the at least one image signal.

22. The ultrasonic imaging system of claim 20, wherein said two-dimensional array is configured and arranged in a substantially planar configuration.

23. The ultrasonic imaging system of claim 20, wherein said two-dimensional array is configured and arranged in a substantially cylindrical configuration.

24. The ultrasonic imaging system of claim 20, wherein said two-dimensional array is configured and arranged in a substantially convex configuration.

25. The ultrasonic imaging system of claim 24, wherein said convex configuration includes substantially equal lateral and longitudinal dimensions.

* * * * *